United States Patent
Bell et al.

[11] Patent Number: 5,295,489
[45] Date of Patent: Mar. 22, 1994

[54] ENDOTRACHEAL TUBE/STETHOSCOPE/THERMISTOR COMBINATION

[75] Inventors: Floyd R. Bell, Portsmouth, Ohio; Thomas H. McKay, Versailles, Ky.

[73] Assignee: Medi-Tube Corporation, Lexington, Ky.

[21] Appl. No.: 811,531

[22] Filed: Dec. 20, 1991

[51] Int. Cl.⁵ ............................................. A61B 5/02
[52] U.S. Cl. ..................................... 128/715; 128/736
[58] Field of Search .......................... 128/715, 773, 736

[56] References Cited

U.S. PATENT DOCUMENTS

| | | | |
|---|---|---|---|
| Re. 31,377 | 9/1983 | Mylrea et al. | 128/642 |
| 3,734,094 | 5/1973 | Calinog | 128/642 |
| 4,263,921 | 4/1981 | Trugillo | 128/736 |
| 4,304,239 | 12/1981 | Perlin | 128/642 |
| 4,383,534 | 5/1983 | Peters | 128/671 |
| 4,917,107 | 4/1990 | Bell et al. | 128/715 |
| 4,967,759 | 11/1990 | Teves | 128/715 |
| 5,029,591 | 7/1991 | Teves | 128/715 |

*Primary Examiner*—William E. Kamm
*Assistant Examiner*—Scott M. Getzow
*Attorney, Agent, or Firm*—King and Schickli

[57] ABSTRACT

An endotracheal tube, stethoscope, and thermistor combination is provided to allow simultaneous patient ventilation, vital sounds monitoring, and body core temperature monitoring by a single instrument. The tube includes an inflation cuff adjacent the distal end and a longitudinal pressure conduit to inflate the cuff to seal against the trachea wall. An audio cuff extends at least partially coextensive and concentrically with the inflation cuff and has sufficient resiliency to vibrate in response to the patient's vital sounds. Audio ports face toward the left side, and thus the heart of the patient to receive heart sounds most directly. A thermistor extends longitudinally along the posterior wall of the preferably bowed tube for contact of the transducer with the patient's mucous membrane for accurately monitoring of the body core temperature. The inflation cuff comprises a highly flexible bulb in direct contact with the trachea wall and the audio cuff is a sleeve inside the bulb and spaced peripherally from the tube to allow vibration. The sleeve has integral ribs so as to be sufficiently stable to maintain the desired spacing and thus assure maximum sound pick-up. A pressure conduit and audio conduit extend along the side wall and open into the inflation and audio cuffs, respectively.

15 Claims, 2 Drawing Sheets

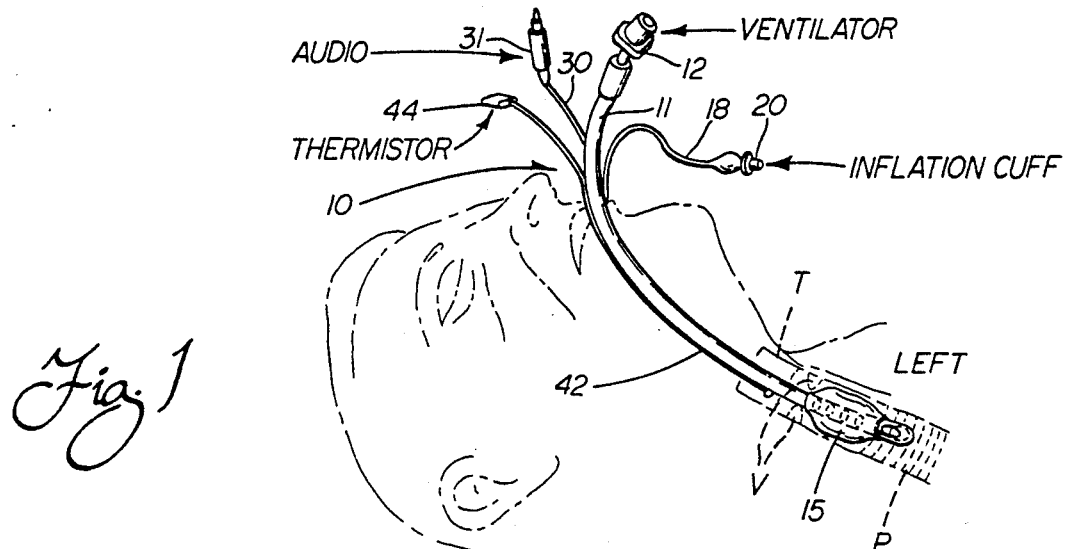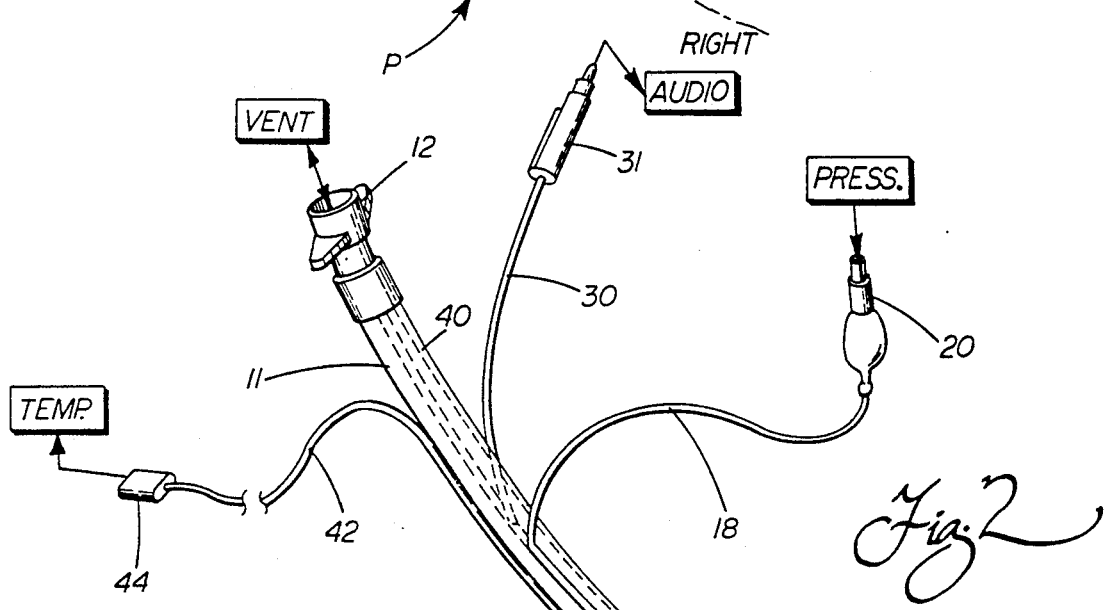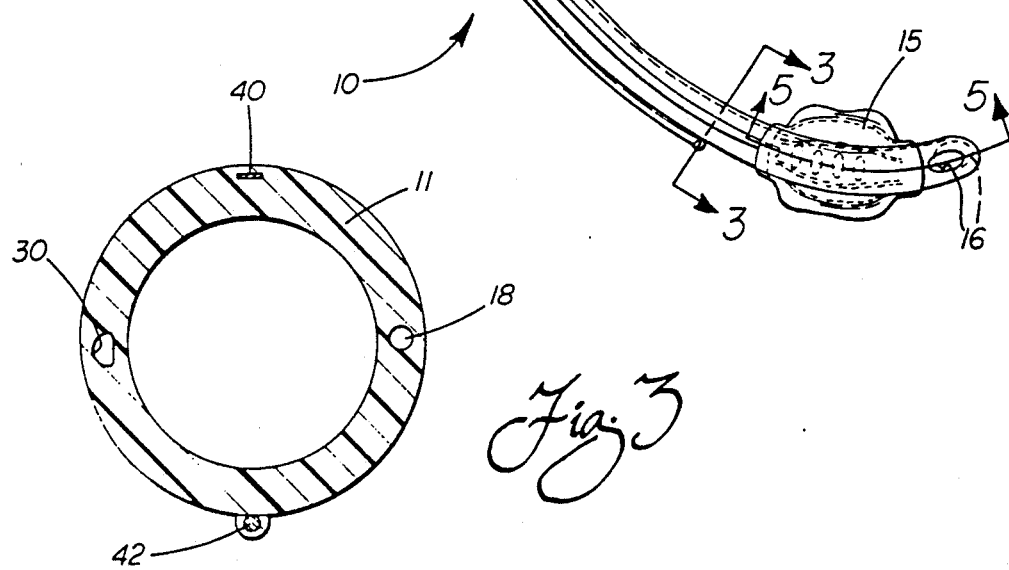

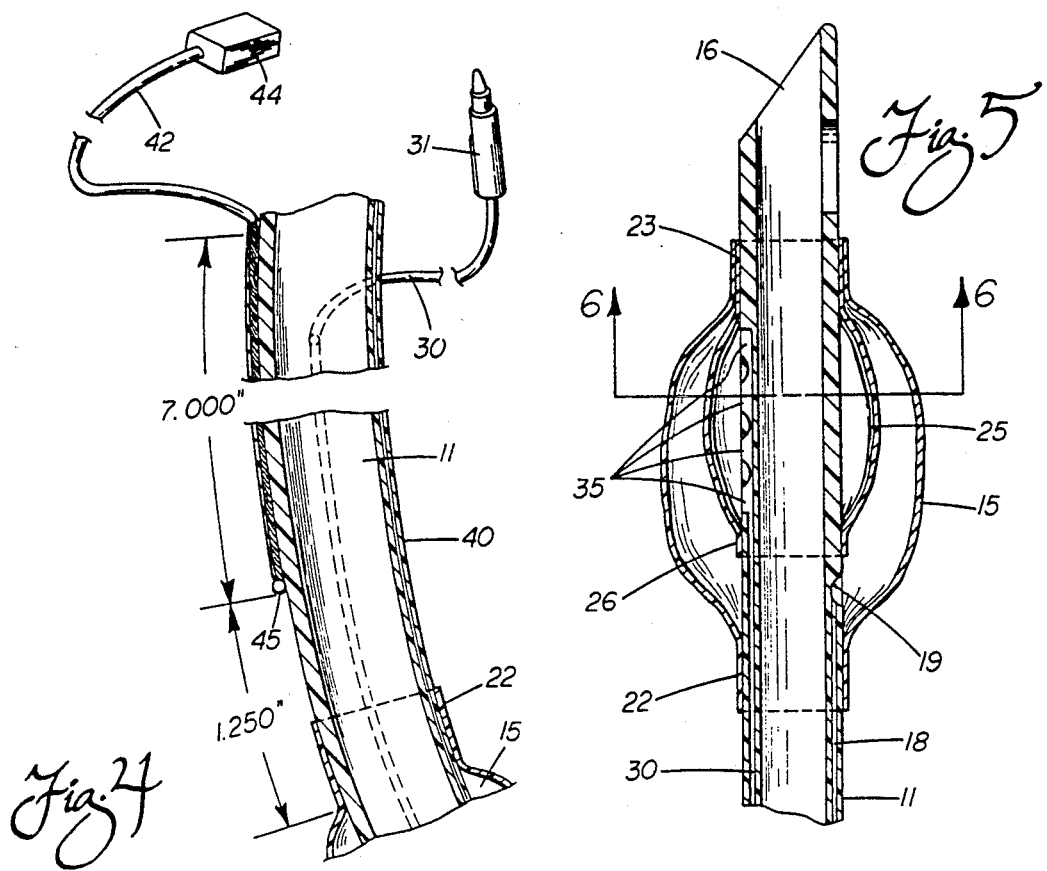
Fig. 4
Fig. 5
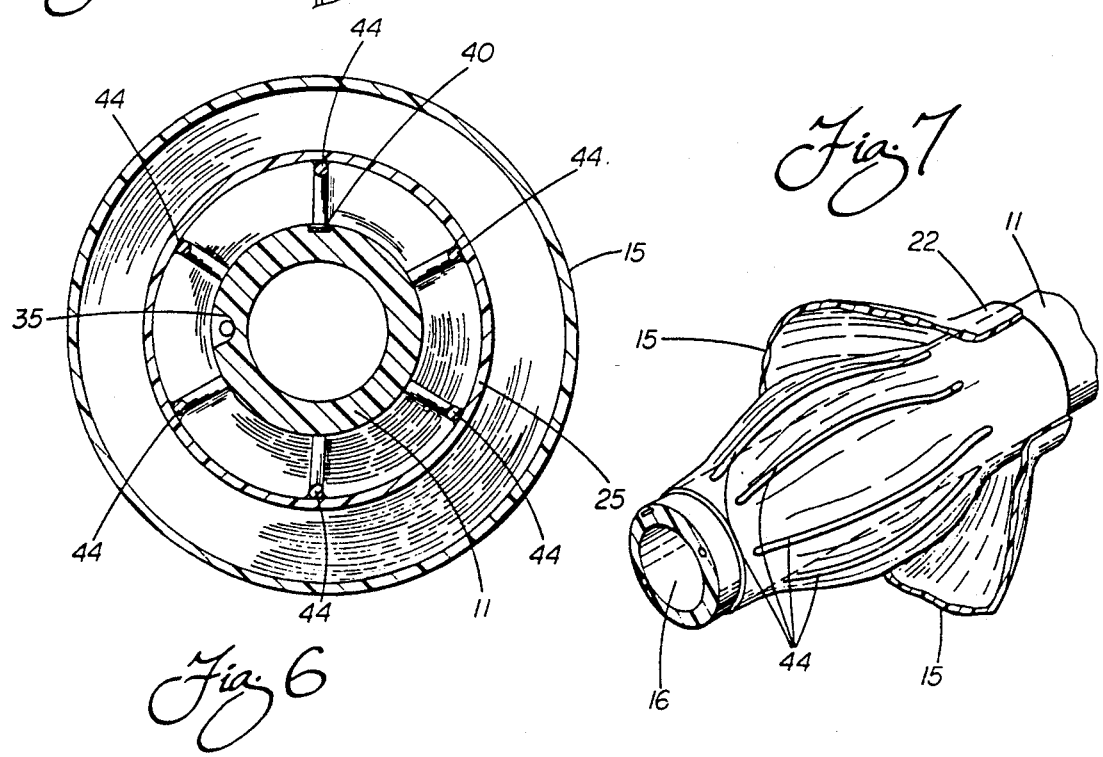
Fig. 6
Fig. 7

ENDOTRACHEAL TUBE/STETHOSCOPE/THERMISTOR COMBINATION

BACKGROUND OF THE INVENTION

The present invention relates to the construction of an endotracheal tube for applying anesthetic gases and/or supplying oxygen to a patient, and more particularly to an endotracheal tube combined with an integral stethoscope and thermistor to allow more efficient monitoring of the patient's vital sounds and body core temperature during an operation.

BACKGROUND ART

During surgical operations, a preferred method of ventilating a patient, including applying an anesthetic to the patient, involves the use of a tube extending into the trachea of the patient. The tube is inserted through the throat of the patient to a location in the trachea just below the vocal cords. At this location, an inflation cuff is pressurized in order to seal against the walls of the trachea. When this sealing is accomplished, the desired intrapulmonary pressure can be established by the introduction of the appropriate gases. These gases are administered through a ventilator machine attached to the proximal end of the tube.

In prior U.S. Pat. Nos. 4,607,643 and 4,917,107, an endotracheal tube/stethoscope combination is disclosed to allow simultaneous patient ventilation and monitoring of vital sounds by a single instrument so as to minimize the number of invasive instruments in the body during an operation. The endotracheal tube, disclosed therein, includes a cuff adjacent the distal end and at least one longitudinal conduit to inflate the cuff to seal and/or pick up sounds. A preferred embodiment includes an audio cuff extending at least partially coextensive and concentrically with a separate inflation cuff and is designed to vibrate in response to the patient's vital sounds. The inflation cuff comprises a highly flexible bulb in direct contact with the trachea wall and the audio cuff is a sleeve inside the bulb and spaced peripherally from the tube to allow sound-induced vibration. The sleeve may be foam-filled to maintain the even spacing with respect to the tube upon inflation of the bulb. The pressure conduit of the preferred embodiment extends longitudinally along the tube and opens into communication with the inflation cuff. An audio conduit extends along the side wall and opens through a plurality of ports forming an audio manifold into the audio cuff.

The endotracheal tube/stethoscope combination of the aforementioned patents, however, suffers from several disadvantages. Chief among these disadvantages is the inability to accurately and consistently position the audio ports, contained within the audio cuff, to receive the patient's vital sounds. In this regard, it has been discovered that to be most efficient the ports should face toward the left side of the patient toward the heart. This is shown to improve the reception of the heart sounds by providing for a more direct, unobstructed path for the sound to travel. An additional disadvantage is the susceptibility of an audio cuff, positioned within an inflation cuff, to partially collapse upon pressurization of the inflation cuff so that its reception of the patient's vital sounds is impaired. While the aforementioned patents suggest filling the sleeve with foam to maintain its spacing, such foam-filling may increase the expense of manufacturing. Under some conditions, the foam may actually damp the transmission of the patient's vital sounds.

Furthermore, with the endotracheal tube/stethoscope combination, the anesthetist must not only operate and monitor the endotracheal tube/stethoscope combination, but also monitor a separate thermometer to determine the patient's body core temperature during the operation. In addition to monitoring the two separate instruments, the anesthetist must ensure that they are maintained in their proper location. With multiple instruments, there is a greater likelihood of the thermometer or other vital instrument being disturbed by the others, such as the doctor performing the operation, or the unexpected movement of the patient's body.

DISCLOSURE OF THE INVENTION

Thus, with the above needs for improvement in focus, it is a primary object of the present invention to provide a simplified, combined endotracheal tube, stethoscope, and temperature transducer to allow more efficient introduction of anesthetics or the like to a patient and simultaneous monitoring of the vital sounds and the core body temperature of the patient.

It is another object of the present invention to provide an endotracheal tube/stethoscope/thermistor combination providing greatly increased ease of handling and use by the anesthetist.

It is still another object of the present invention to provide an instrument for administering anesthetics and simultaneously monitoring vital sounds and core body temperature that is immediately ready to use after intubation and easier to properly insert and to maintain in the proper position throughout the operation, and to allow for a more direct path for the transmission of the patient's vital sounds.

It is another object of the present invention to provide a combined tracheal tube, stethoscope, and thermistor that can be inexpensively manufactured and reduce the overall expense involved in instruments and related apparatus needed by an anesthetist.

It is still another object of the present invention to provide an endotracheal tube with an inflation cuff for sealing the trachea, a reinforced audio cuff forming a stethoscope transducer within the inflation cuff, and a thermistor forming a temperature transducer positioned along the posterior face of the tube.

Additional objects, advantages and other novel features of the invention will be set forth in part in the description that follows, and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects, and in accordance with the purposes of the present invention as described herein, an improved assembly for use by an anesthetist during an operation for providing endotracheal ventilation, monitoring vital sounds by stethoscope, and monitoring core body temperature by thermistor is provided. The assembly includes a trachea tube, an inflation cuff located at the distal end surrounding the tube, means for pressurizing the cuff to seal against the trachea wall, an audio cuff having sufficient resiliency to vibrate to monitor patient vital sounds, and a thermistor positioned along the posterior side wall of the tube to permit monitoring of the patient's core body temperature. The tube has audio ports opening into the audio cuff and facing the left side for improved heart sounds reception. The preformed bow of the tube and an x-ray marker extending along the anterior side wall of the tube allows the thermistor to be consistently positioned toward the rear of the patient and the audio ports to be consistently positioned to face toward the left side of the patient. This assures the accurate temperature pick-up and improved reception of the heart sounds, respectively.

Also, in the preferred embodiment, the audio cuff includes longitudinal ribs to resist collapse against the tube, to further improve the sound quality.

A pressure conduit extends longitudinally inside the wall of the tube with a mouth opening into the inflation cuff. A pressure connector adjacent the proximal end is provided for connection to a suitable pressure source. A similar conduit extends longitudinally along the inside of the wall of the tube for transmission of the sounds from the audio cuff. An audio connector adjacent the proximal end is provided for direct connection to a stethoscope headset. The thermistor positioning along the posterior wall of the tube allows direct contact with the patient's mucous membrane upon intubation to provide the increased accuracy in monitoring the patient's core body temperature. A thermistor connector adjacent the proximal end is provided for direct connection to an appropriate temperature monitoring instrument. The endotracheal tube includes a connector also adjacent the proximal end for direct connection to a ventilator for applying the anesthetic gases/oxygen to the patient.

The audio conduit opening through the plurality of ports forms an audio manifold inside the audio cuff. The ports or manifold are positioned a consistent angular distance from the x-ray marker such that by positioning the x-ray marker toward the front of the patient, the audio ports face toward the left side of the patient to allow the desired more direct path for the heart sounds to travel.

The audio cuff itself includes a flexible plastic sleeve, having a plurality of internal, longitudinal ribs, slightly spaced from the tube to allow vibration in response to the vital sounds. The ribbed sleeve is sufficiently stable to maintain the spacing even upon inflation of the inflation cuff. In contrast, the inflation cuff is formed by a highly flexible bulb so as to provide acceptable sealing action in the trachea with minimum pressure so as to enhance the audio volume from the audio cuff, and also lessen the possibility of excess pressure that could harm the delicate mucous membranes of the trachea.

Since the inflation cuff totally encompasses the inner audio cuff, there is a desirable reduction in uncontrolled vibration and resonating of the audio cuff to provide better sound definition. The inflation cuff also provides the optimum seal around the trachea to maintain the desired intrapulmonary pressure. The breath sounds are picked up by the audio cuff directly from the in and out flow of gases along the tube and the heart sounds are picked up directly by transmission through the inflation cuff, pressurized gas and audio cuff. With the combined endotracheal tube, stethoscope, and thermistor of the invention, the anesthetist is able to more easily hear and distinguish the breath and heart sounds. This is so since the sound transducers are directed closer to the source by the audio ports being positioned toward the patient's left side. The heart sounds travel a more direct path to the audio cuff.

Still other objects of the present invention will become readily apparent to those skilled in this art from the following description, wherein there is shown and described in more detail the preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

FIG. 1 is a perspective view of the endotracheal tube/stethoscope/thermistor combination with identification of the supply and monitoring connections and illustrating the use on a patient;

FIG. 2 is an enlarged perspective view of the endotracheal tube/stethoscope/thermistor combination of the present invention connected to well known supply/monitoring devices;

FIG. 3 is a cross-sectional view taken along lines 3—3 of FIG. 2 showing the pressure conduit, audio conduit, thermistor, and alignment marker;

FIG. 4 is a longitudinal cross-sectional view of the portion of the endotracheal tube/stethoscope/thermistor combination of the present invention, broken away for clarity and showing the positioning of the thermistor;

FIG. 5 is a cross-sectional view taken along line 5—5 of FIG. 2 along the longitudinal axis adjacent the distal end of the assembly and showing the leftwardly directed audio ports;

FIG. 6 is a cross-sectional view along line 6—6 of FIG. 5 showing the audio cuff having integral ribs within the inflation cuff and one port of the audio manifold; and FIG. 7 is a perspective view of the distal end of the endotracheal tube/stethoscope/thermistor combination with the inflation cuff partially broken away to show the integral ribs of the audio cuff.

BEST MODE OF CARRYING OUT THE INVENTION

Reference is now made to FIG. 1, illustrating the manner in which the combined endotracheal tube/stethoscope/thermistor assembly 10 is utilized on a patient P, shown in phantom outline. Included in the assembly 10 is an endotracheal tube 11, best shown in FIG. 2, with a connector 12 for connection to a ventilator, which is not illustrated. The distal end of the tube 11 includes an inflation cuff 15 surrounding the tube 11 and an adjacent opening 16 for supplying the anesthetic gases (such as nitrous oxide) and oxygen to the pulmonary system of the patient.

The endotracheal tube 11, as well as the other components of the assembly 10, are made of surgical grade plastic in accordance with well known principles, and as more fully described in the aforementioned patents.

The inflation cuff 15 is inflated by pressurized gas, such as pressurized ambient air. This gas is supplied through a pressure conduit 18 extending along the wall of the tube 11, as best shown in FIG. 5. The distal end of the pressure conduit 18 opens into the chamber within the cuff 15 through a mouth 19. As shown in FIG. 2, the conduit 18 emerges from the tube 11 at a location partially along the tube's length and is provided with a pressure connector 20 at the proximal end. The pressure connector 20 is connected to a suitable pressure source and upon activation the pressurized gas fills the chamber and inflates the cuff 15 (see FIG. 5).

In the preferred embodiment, the cuff 15 takes the form of a bulb that is substantially concentric with the tube 11. The two ends of the cuff 15 are heat sealed around the outside against the tube at heat seal areas 22, 23, thus forming a gas tight chamber. An audio cuff 25 is formed on the tube 11 in the same region. Specifically, the audio cuff 25 is at least partially coextensive with the inflation cuff 15 along the tube 11. The cuff 25 is preferably a sleeve with one end attached to the tube by sealing under the inflation cuff 15 in seal area 23, and a separate seal area 26 inside the inflation chamber (see FIG. 5).

As will be thus realized, in the preferred embodiment, the audio cuff 25 is positioned wholly within the inflation cuff 15. Running to the audio cuff 25 is an audio conduit 30 (see FIGS. 4 and 5). As is evident in FIG. 2, the conduit is integral with the side wall of the tube 11 to a mid-point where the conduit 30 emerges, finally terminating at the proximal end in audio connector 31. A suitable headset, not shown, is attached to audio connector 31.

The opening of the audio conduit 30 to the chamber within the audio cuff 25 takes the form of a plurality of spaced ports 35 forming in effect an audio manifold (see FIG. 5). With this arrangement, upon vibration of the audio cuff 25, the sound waves can freely enter the manifold, travel up through the conduit 30 and connector 31 to the headset of the anesthetist. As will be apparent and as proven in commercial tubes, this direct sound detection and transmission works well and is a significant advance of the prior art.

In order to provide even better performance for sensing the vital sounds, a more direct path for heart sounds to propagate to the manifold is provided. The preformed bow of the tube positions the manifold with the ports 35 facing toward the left side of the patient. An x-ray marker 40 is formed on the front or anterior side wall of tube 11. The x-ray marker 40 is spaced approximately 90° from the audio conduit 30 and the ports 35, as shown in FIG. 3. By inserting the tube 11 with the bow matching the curvature of the tracheal and such that the x-ray marker 40 is positioned toward the front of the patient P, the audio conduit 30 and, more importantly, the audio ports 35 are positioned toward the left side. As will be realized, this positioning provides a more direct path for sounds emanating from the heart to the audio ports 35.

A thermistor 42 is positioned along the rear or posterior side wall of tube 11, oppositely disposed on the tube from the x-ray marker 40, as shown in FIG. 3. The thermistor 42 is attached to the side wall of the tube 11, or threaded through a conduit, until a point substantially midway where the thermistor lead separates from the tube 11, finally terminating at the proximal end in a thermistor connector 44 (see FIGS. 2 and 4). The thermistor connector 44 is connected to an appropriate temperature monitor, which is not illustrated. To ensure a proper sensing location within the patient, transducer 45 at the distal end of the thermistor 42 is positioned above the inflation cuff 15, as illustrated in FIGS. 1 and 4. In the preferred embodiment, the thermistor 42 terminates approximately 1.250 inches above the lower extent of the seal area 22 of the inflation cuff 15.

The thermistor transducer comes in contact with the mucous membrane at this preferred location so as to accurately measure the patient's core body temperature. The bow of the tube 11 is preferably such that gentle contact is maintained. In actual tests, the thermistor 42 provides a reading to within 0.2° F. to 0.8° F., typically within 0.5° F., of the patient's core body temperature.

In use, the tube 11 is inserted into the mouth of the patient P, substantially as shown in FIG. 1, with the x-ray marker 40 positioned toward the front so that the audio ports 35 face toward the patient's left side. The tube 11 and the deflated cuff 15 travel easily through the throat T and past the vocal cords V into the trachea R. With the cuff 15 now in position, the pressure source 21 can be immediately activated, the cuff 15 inflated, and the anesthetic gases/oxygen immediately administered.

The distal tip of the tube 11 is in this position well above the carina between the left bronchus and the right bronchus. With the trachea thus sealed, the pulmonary pressure can be properly established and maintained for the duration of the operation.

Thus, in the preferred embodiment of the invention, the inflation cuff 15 directly engages the peripheral wall of the trachea R. From this direct engagement and positioning of the audio ports 35 toward the left side of the patient P, heart sounds emanating from within the body from surrounding arteries and the heart itself are transmitted directly into the chamber formed by the cuff 15. The pressurized gas in turn transmits these pulsations to the audio cuff 25; the sound waves then traveling through the manifold of ports 35, the conduit 30 and eventually to the stethoscope of the anesthetist. Advantageously, the audio cuff 25 faithfully picks up the pulsating sounds free of noise background. The arrangement substantially reduces uncontrolled vibration and resonating that occurs in other instances where a separate stethoscope is used.

In addition to monitoring the heart sounds, the cuff 25 allows monitoring of the bi-directional breath sounds as the gases pass back and forth through the inside of the tube 11. It is proven to be highly advantageous to have both vital sounds of the patient P being picked up by the same audio transducer and now the anesthetist can faithfully monitor both sounds, as well as the patient's core body temperature provided by the thermistor 42, in order to assure maximum safety of the patient.

The audio cuff 25 is formed of a flexible plastic sleeve and is slightly spaced from the tube 11, as shown in FIGS. 5 and 6, in order to allow vibration in response to the vital sounds. The audio cuff 25 has a plurality of integral ribs 44 formed upon the internal surface of the sleeve between the seal areas 23, 26 (see FIGS. 6 and 7). The ribs 44 are preferably positioned to be substantially parallel with the longitudinal axis of the tube 11. The ribs 44 assist in stabilizing the sleeve such that appropriate spacing is maintained about the periphery of the tube 11 upon pressurization of the inflation cuff 15. The thin sections of the sleeve between the ribs 44 are highly flexible, and freely vibrate to generate the sound representative of the heart beats. The plastic bulb forming the inflation cuff 15 is highly flexible over its entire extent. The flexibility assures optimum sealing engagement with the wall of the trachea R using minimum gas pressure. This fact also assists in keeping the audio cuff 25 from collapsing against the outer wall of the tube 11.

In summary, a combined endotracheal tube/stethoscope/thermistor assembly 10 is provided, that is simple in construction and provides improved performance. The heart and breath sounds are enhanced so as to be easier to hear and distinguish. The audio cuff 25 picks up the heart sounds that arrive by the most direct route with the ports 35 facing the left side of the patient P.

The audio cuff 25 formed with internal ribs 44 is sufficiently stable to maintain the spacing from the tube 11, whereby both heart and breath sounds are maintained during an operation without a tendency to collapse, as has been a problem in the past. Uncontrolled vibration and resonating of the sounds are essentially eliminated. The core body temperature is monitored by the transducer 45 directly engaging the mucous membrane along the posterior wall of the tracheal. The positioning at approximately 1.250 inches above the lower extent of the seal area 22 where the sealing chamber of the cuff 15 starts assures a position adjacent the vocal cords V (see FIG. 1) for maximum accuracy; that is, within about 0.5° F. of core temperature.

The foregoing description of a preferred embodiment of the invention has been presented for purposes of illustration and description. It is not intended to be exhaustive or to limit the invention to the precise form disclosed. Obvious modifications or variations are possible in light of the above teachings. For example, the inflation cuff may, if desired, be positioned inside the audio cuff, or integral therewith, to provide direct engagement of the audio cuff with the trachea. In this instance, the ribbed audio cuff may be slightly pressurized and/or foam-filled to provide resiliency to enhance the vibrating action. It will thus be realized that the preferred embodiment was chosen and described to provide the best illustration of the principals of the invention and its practical application to thereby enable one of ordinary skill in the art to utilize the invention and various embodiments and with various modifications as are suited to the particular use contemplated. It is intended that the scope of the invention be defined by the claims appended hereto.

We claim:

1. An assembly for providing endotracheal ventilation, vital sound monitoring by stethoscope, and body core temperature monitoring in a patient comprising:
   a. a tracheal tube having a preformed bow for matching the curvature of the trachea and a distal end for positioning in the trachea of the patient;
   b. means for substantially peripherally sealing the assembly against the tracheal wall adjacent the distal end of the tube inserted in the trachea;
   c. means for providing ventilation to the trachea through said tube;
   d. audio means extending along the tube at least partially coextensive with said sealing means and having sufficient resiliency to vibrate in response to patient vital sounds to permit monitoring during ventilation; and
   e. a temperature transducer on said tube positioned and exposed to the outside of said tube along the outside of the bow of the tube to be substantially in contact with the mucous membrane of the trachea toward the back of the patient to permit monitoring of the patient body core temperature during ventilation.

2. The assembly of claim 1, wherein said transducer is a thermistor.

3. The assembly of claim 2, wherein said audio means is formed by a flexible audio cuff, an opening to the audio cuff is provided by port means forming an audio manifold adjacent said distal end of said tube.

4. The assembly of claim 3, wherein said port means is directed toward the left side of the patient and toward the heart for substantially direct path pick-up of heart sounds.

5. The assembly of claim 1, wherein the temperature transducer is located on said tube so as to be positioned adjacent the vocal cords of the patient and about 1.25 inches above the sealing means.

6. An assembly for providing endotracheal ventilation and vital sound monitoring by stethoscope in a patient comprising:
   a. a tracheal tube having a preformed bow for matching the curvature of the trachea and a distal end for positioning in the trachea of the patient and including a side wall;
   b. means for substantially peripherally sealing the assembly against the tracheal wall adjacent the distal end of the tube inserted in the trachea;
   c. means for providing ventilation to the trachea through said tube;
   d. audio means extending along the tube at least partially coextensive with said sealing means and having sufficient resiliency to vibrate in responsive to patient vital sounds to permit monitoring during ventilation; and
   e. port means opening to said audio means positioned approximately 90° from the outside of the bow relative to the tube of the tube and directed toward the left side of the patient and the heart for substantially direct path pick-up of heart sounds.

7. The assembly of claim 6, wherein is provided a marker extending along said tube, the marker being positioned approximately 90° form said port means and along the inside of the bow to assure proper alignment toward said heart.

8. An assembly for providing endotracheal ventilation and vital sound monitoring by stethoscope in a patient comprising:
   a. a tracheal tube having a distal end for positioning in the trachea of the patient and including a side wall;
   b. means for substantially peripherally sealing the assembly against the tracheal wall adjacent the distal end of the tube inserted in the trachea;
   c. means for providing ventilation to the trachea through said tube;
   d. audio means extending along the tube at least partially coextensive with said sealing means and having sufficient resiliency to vibrate in response to patient vital sounds to permit monitoring during ventilation;
   e. port means opening to said audio means and directed toward the left side of the patient and the heart for substantially direct path pick-up of heart sounds; and
   f. said audio means including a cuff formed by a plastic sleeve extending around the periphery of the tube, said sleeve having a plurality of integral stiffening ribs to resist collapse against said tube.

9. The assembly of claim 5, wherein the ribbed sleeve is slightly spaced from said tube providing sufficient spacing to allow vibration in response to said vital sounds.

10. The assembly of claim 9, wherein the ribs extend longitudinally along said sleeve.

11. An assembly for providing endotracheal ventilation, vital sound monitoring by stethoscope, and body core temperature monitoring in a patient comprising:
   a. a tracheal tube having a distal end for positioning in the trachea of the patient;
   b. means for substantially peripherally sealing the assembly against the tracheal wall adjacent the distal end of the tube inserted in the trachea;
   c. means for providing ventilation to the trachea through said tube;
   d. audio means extending along the tube at least partially coextensive with said sealing means and having sufficient resiliency to vibrate in response to patient vital sounds to permit monitoring during ventilation; and
   e. a temperature transducer on said tube and exposed to the outside said tube to be substantially in contact with the mucous membrane of the tracheal to permit monitoring of the patient body core temperature during ventilation; said audio means comprising a cuff formed by a plastic sleeve extending around the periphery of the tube, said sleeve having a plurality of integral stiffening ribs to resist collapse against said tube.

12. An assembly for providing endotracheal ventilation, vital sound monitoring by stethoscope, in a patient comprising:
   a. a tracheal tube having a distal end for positioning in the trachea of the patient;
   b. means for substantially peripherally sealing the assembly against the tracheal wall adjacent the distal end of the tube inserted in the trachea;
   c. means for providing ventilation to the trachea through said tube; and
   d. audio means extending along the tube at least partially coextensive with said sealing means and having sufficient resiliency to vibrate in response to patient vital sounds to permit monitoring during ventilation; said audio means comprising a cuff formed by a plastic sleeve extending around the periphery of the tube, said sleeve having stiffening means to resist collapse against said tube.

13. The assembly of claim 12, wherein said stiffening means includes at least one separate stiffening rib formed integrally with said sleeve.

14. The assembly of claim 13, wherein said rib extends substantially in the longitudinal direction of said tube.

15. The assembly of claim 14, wherein a plurality of ribs forms the stiffening means.

* * * * *